(12) United States Patent
Kim et al.

(10) Patent No.: US 11,446,234 B2
(45) Date of Patent: Sep. 20, 2022

(54) ***LACTOBACILLUS REUTERI* CH53 STRAIN HAVING HIGH PRODUCTIVITY OF 1,3-PROPANEDIOL FROM GLYCEROL AND USES THEREOF**

(71) Applicant: ACTIVON CO., LTD., Chungcheongbuk-do (KR)

(72) Inventors: Chul Ho Kim, Daejeon (KR); Baek Rock Oh, Daejeon (KR); Jeong-Woo Seo, Daejeon (KR); Sun-Yeon Heo, Daejeon (KR); Jung Hyun Ju, Daejeon (KR)

(73) Assignee: ACTIVON CO., LTD., Chungcheongbuk-Do (KR)

( * ) Notice: Subject to any disclaimer, the term of this patent is extended or adjusted under 35 U.S.C. 154(b) by 692 days.

(21) Appl. No.: 16/461,596

(22) PCT Filed: Nov. 27, 2017

(86) PCT No.: PCT/KR2017/013587
§ 371 (c)(1),
(2) Date: May 16, 2019

(87) PCT Pub. No.: WO2018/101684
PCT Pub. Date: Jun. 7, 2018

(65) Prior Publication Data
US 2019/0365640 A1 Dec. 5, 2019

(30) Foreign Application Priority Data

Nov. 29, 2016 (KR) .................. 10-2016-0160302

(51) Int. Cl.
| | | |
|---|---|---|
| *C12P 7/18* | (2006.01) | |
| *C12N 1/20* | (2006.01) | |
| *A61K 8/99* | (2017.01) | |
| *A61Q 19/00* | (2006.01) | |

(52) U.S. Cl.
CPC .............. *A61K 8/99* (2013.01); *A61Q 19/007* (2013.01); *C12N 1/20* (2013.01); *C12P 7/18* (2013.01)

(58) Field of Classification Search
None
See application file for complete search history.

(56) References Cited

FOREIGN PATENT DOCUMENTS

| KR | 10-2004-0048620 A | 6/2004 |
| KR | 10-2010-0063585 A | 6/2010 |
| KR | 10-2011-0129070 A | 12/2011 |
| KR | 10-2013-0011343 A | 1/2013 |

OTHER PUBLICATIONS

Ju et al., "Enhancement of 1,3-propanediol production from industrial by-product by Lactobacillus reuteri CH53", Microb. Cell Fact. 19:6, 2020, 10 pages (Year: 2020).*
International Search Report for PCT/KR2017/013587 dated Aug. 3, 2018.
Jyotsna Jolly et al., "Biosynthesis of 1,3-propanediol from glycerol with Lactobacillus reuteri: Effect of operating variables", Journal of Bioscience and Bioengineering, vol. 118, No. 2, 2014.
Hema Vaidyanathan et al., "Glycerol conversion to 1,3-Propanediol is enhanced by the expression of a heterologous alcohol dehydrogenase gene in Lactobacillus reuteri", AMB Express, vol. 1, thesis No. 37, 2011.
Maria Antonietta Ricci et al., "Improved 1,3-Propanediol Synthesis from Glycerol by the Robust Lactobacillus reuteri Strain DSM 20016", Journal of Microbiology and Biotechnology, vol. 25 No. 6, pp. 893-902, 2015.

* cited by examiner

*Primary Examiner* — David Steadman
(74) *Attorney, Agent, or Firm* — The PL Law Group, PLLC

(57) ABSTRACT

*Lactobacilus reuteri* CH53 strain has high productivity of 1,3-propanediol from glycerol and uses thereof. It is confirmed that *Lactobacilus reuteri* CH53 strain is capable of converting at very high yield glycerol or crude glycerol to high-concentration 1,3-propanediol. Since *Lactobacillus reuteri* CH53 strain of the present invention capable of producing large amounts of 1,3-propanediol is one kind of lactic acid bacteria that are safe for humans (GRAS, Generally Recognized As Safe), when it is used for producing 1,3-propanediol from crude glycerol, it would be very advantageously used, unlike existing GMO strains, in related industries from the viewpoint of safety or environment and also providing an advantage of recycled use of resources.

1 Claim, 2 Drawing Sheets
Specification includes a Sequence Listing.

LACTOBACILLUS REUTERI CH53 STRAIN HAVING HIGH PRODUCTIVITY OF 1,3-PROPANEDIOL FROM GLYCEROL AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/013587, filed on Nov. 27, 2017, which claims priority to the benefit of Korean Patent Application No. 10-2016-0160302 filed in the Korean Intellectual Property Office on Nov. 29, 2016, the entire contents of which are incorporated herein by reference.

STATEMENT REGARDING GOVERNMENT SPONSORED APPLICATION

This application is financially supported by the 2016 Commercialization Project for Promising Technologies of the government of the Republic of Korea.

TECHNICAL FIELD

The present invention relates to *Lactobacillus reuteri* CH53 strain having high productivity of 1,3-propanediol from glycerol and uses thereof.

BACKGROUND ART

As a major by-product of the current process for producing biodiesel, crude glycerol is generated in an amount which corresponds to about 10% (w/w) of the entire production. As the crude glycerol exhibits an influence on traditional market price of glycerol and cannot be directly released into an environment, it now becomes a critical environmental issue including processing costs. Thus, a method for conversion into an industrially valuable material like fuels and physiologically active materials by using low priced crude glycerol is actively developed.

According to fermentation by microorganism, glycerol can be converted to various chemical materials, and representative examples thereof include 1,3-propanediol. 1,3-Propanediol is used for various applications including fibers like highly functional clothing, carpet, and fabric for an automobile, plastic films, cosmetics, and the like. In particular, it is commercially available as "Propanediol", which is a raw material of cosmetics, and it is known to have a more favorable moisturizing effect and anti-microbial effect than 1,3-butylene glycol which is used as a raw material of cosmetics in related art. At present moment, because 1,3-propanediol is mostly produced by using a recombinant microbial strain (*Escherichia coli*, *Klepsiella*, or *Clostridium*), it has limitations of GMO, and there is high reluctant feel in the market about using it.

Under the circumstances, the inventors of the present invention made an effort to solve those problems, and, as a result, succeeded in newly isolating *Lactobacillus reuteri* CH53 strain, which is a *lactobacillus* strain safe for humans. Furthermore, based on the isolation of *Lactobacillus reuteri* CH53 strain, the inventors can provide a basis of a technique which enables production of 1,3-propanediol in very large amounts from glycerol or crude glycerol.

Meanwhile, in Korean Patent Application Publication No. 2010-0063585, "Mutant blocked in glycerol oxidation pathway for producing 1,3-propanediol" is disclosed, and, in Korean Patent Application Publication No. 2011-0129070, "Method for high-yield production of 3-hydroxypropionic acid from glycerol" is disclosed. However, nothing has been described with regard to *Lactobacillus reuteri* CH53 strain having high productivity of 1,3-propanediol from glycerol and uses thereof as described in the present invention.

SUMMARY

The present invention is devised under the circumstances described in the above, and object of the present invention is to provide *Lactobacillus reuteri* CH53 strain (KCTC13149BP) having high productivity of 1,3-propanediol, which is a key in the technique for producing, via microbial fermentation, 1,3-propandiol as a raw material of high value-added cosmetics (anti-microbial agent and moisturizing agent) by using crude glycerol as an industrial waste.

*Lactobacillus reuteri* CH53 strain (KCTC13149BP) can produce 1,3-propanediol in final amount of 16.3 g/L by consuming 20.1 g/L glycerol, and the production yield compared to glycerol is confirmed to be 0.81 g/g (1,3-propanediol/glycerol), which shows very high conversion rate of 98% when compared to the theoretical production yield (0.83 g/g). It was also confirmed that, according to optimized fed-batch culture, the production amount of 1,3-propanediol is 65.5 g/L (based on 54 hours) and the production per hour is 1.17 g/L/h.

At present moment, because 1,3-propanediol is mostly produced by using a recombinant microbial strain (*Escherichia coli*, *Klepsiella*, or *Clostridium*), it has limitations of GMO and there is high reluctant feel in the market about using it. Accordingly, in the present invention, *Lactobacillus reuteri* CH53 strain, which is lactic acid bacterium, is newly isolated from a strain safe for humans (GRAS, Generally Recognized As Safe), and a production process technique for efficient production of 1,3-propanediol from crude glycerol by using the strain is provided.

To solve the problems that are described above, the present invention provides *Lactobacillus reuteri* CH53 strain (Accession number: KCTC13149BP) having high productivity of 1,3-propanediol from glycerol.

Furthermore, the present invention provides a composition for producing 1,3-propanediol comprising the aforementioned strain or a culture solution thereof as an effective component.

Furthermore, the present invention provides a cosmetic composition for skin moisturization comprising the aforementioned strain or a culture solution thereof as an effective component.

Still furthermore, the present invention provides a method for producing 1,3-propanediol comprising culturing the aforementioned strain.

It is confirmed that *Lactobacillus reuteri* CH53 strain of the present invention has a very remarkable capability of converting glycerol or crude glycerol into 1,3-propanediol. Thus, since *Lactobacillus reuteri* CH53 strain of the present invention, which is capable of producing large amounts of 1,3-propanediol, is one kind of lactic acid bacteria that are safe for humans (GRAS, Generally Recognized As Safe), when it is applied for producing 1,3-propanediol from crude glycerol, unlike existing GMO strains, it would be very advantageously used in related industries from the viewpoint of safety or environment and also providing an advantage of recycled use of resources.

DETAILED DESCRIPTION

Figure 1:
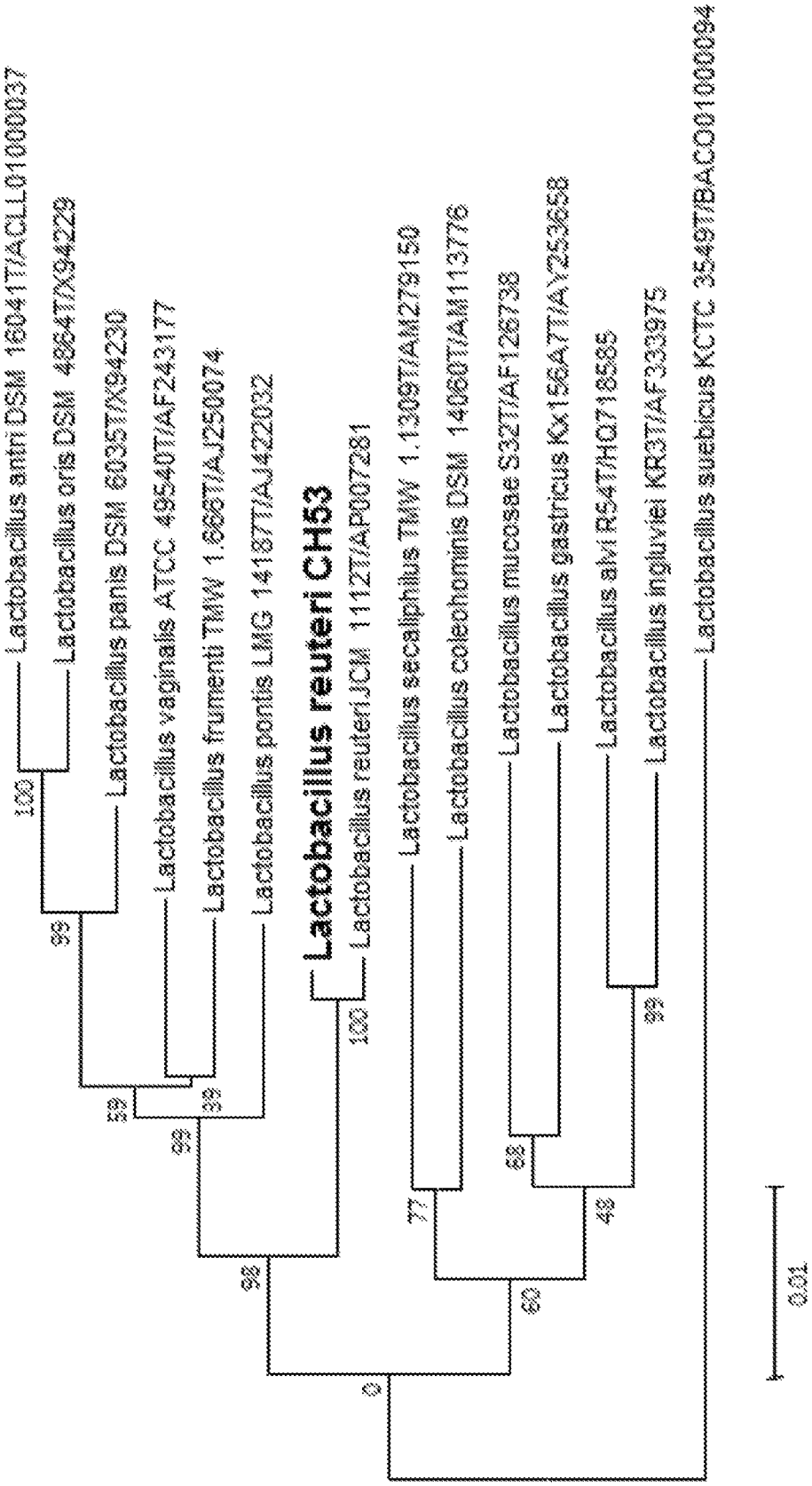
FIG. 1 shows a diagram illustrating the phylogenetic tree of *Lactobacillus reuteri* CH53 strain as lactic acid bacterium, which has been isolated in the present invention.
Figure 2:
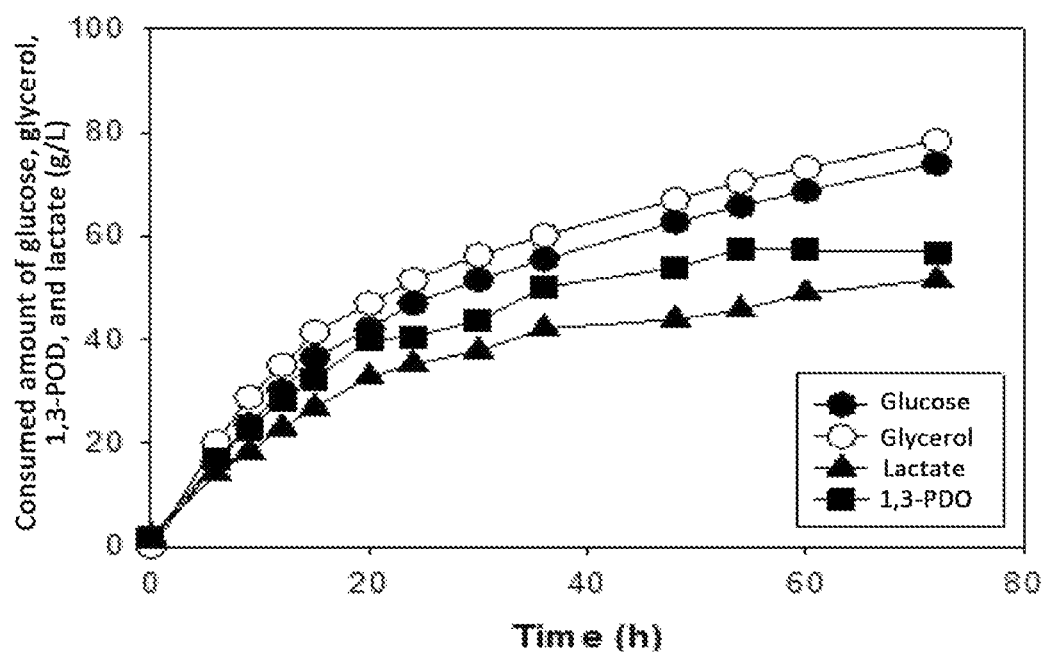
FIG. 2 shows the result of fed-batch culture of *Lactobacillus reuteri* CH53 strain which has been isolated in the present invention, in which the fed-batch culture is carried out by using a 5-liter bioreactor.

In order to achieve the object of the present invention, the present invention provides *Lactobacillus reuteri* CH53 strain (KCTC13149BP) having high productivity of 1,3-propanediol from glycerol.

*Lactobacillus reuteri* CH53 strain (KCTC13149BP) of the present invention consumes 20.1 g/L glycerol to finally produce 16.3 g/L 1,3-propanediol, and the production yield relative to glycerol is determined to be 0.81 g/g (1,3-propanediol/glycerol), which represents very high conversion rate of 98% compared to the theoretical yield (0.83 g/g). It was also confirmed that, according to the optimized fed-batch culture, the production amount of 1,3-propanediol is 65.5 g/L (based on 54 hours) and the productivity per hour is 1.17 g/L/h. Accordingly, the strain was deposited on Nov. 8, 2016 with Korea Research Institute of Bioscience and Biotechnology-KCTC (Accession number: KCTC13149BP).

According to the strain of one embodiment of the present invention, the conversion rate of glycerol into 1,3-propanediol can be 95 to 99%. The conversion rate may be preferably 98%, but it is not limited thereto.

In the present invention, the conversion rate into 1,3-propanediol indicates a percentage value of actual production yield of 1,3-propanediol compared to an addition amount of glycerol in medium for culture of *Lactobacillus reuteri* CH53 strain (KCTC13149BP) of the present invention, in which the percentage value is obtained on the basis of the theoretical production yield of 1,3-propanediol (0.83 g/g).

According to the strain of one embodiment of the present invention, the strain is wherein it has high productivity of 1,3-propanediol per hour. Preferably, the productivity per hour for producing 1,3-propanediol can be 1.0 to 1.3 g/L/h. Most preferably, it can be 1.17 g/L/h, but it is not limited thereto.

The present invention also provides *Lactobacillus reuteri* CH53 strain (Accession number: KCTC13149BP) which has glycerol-to-1,3-propanediol conversion rate of 95 to 99% and has high productivity per hour for producing 1,3-propanediol.

The present invention further provides a composition for producing 1,3-propanediol comprising the aforementioned strain or a culture solution thereof as an effective component.

According to the composition of one embodiment of the present invention, the strain can be *Lactobacillus reuteri* strain, and preferably *Lactobacillus reuteri* CH53 strain (Accession number: KCTC13149BP), but it is not limited thereto.

The present invention further provides a cosmetic composition for skin moisturization comprising the aforementioned strain or a culture solution thereof as an effective component.

The strain of the present invention or a culture solution of the strain is preferably in powder form obtained by freeze drying, but it is not limited thereto.

The cosmetic composition of the present invention may be provided in the form of a solution, a gel, a solid or anhydrous kneaded product, an emulsion obtained by dispersing an oil phase in an aqueous phase, a suspension, a microemulsion, a microcapsule, a fine granule, an ionic liposome, a non-ionic vesicle dispersion, a crème, a skin lotion, a lotion, a powder, an ointment, an essence, a spray, or a concealer stick. It may be also prepared in the form of a foam or an aerosol composition which further contains a compressed propellant.

Furthermore, the cosmetic composition may also contain, in the strain of the present invention or a culture solution of the strain, a supplementary agent that is typically used in the field of cosmetics like an organic solvent, a dissolving agent, a concentrating agent, a gelling agent, a softening agent, an anti-oxidant, a suspending agent, a stabilizing agent, a foaming agent, an aromatic agent, a surfactant, water, an ionic or non-ionic emulsifying agent, a filler, a metal ion sequestering agent, a chelating agent, a preservative, a vitamin, a wetting agent, an essential oil, a dye, a pigment, a hydrophilic or lipophilic activating agent, a lipid vesicle and other optional components commonly used for cosmetics.

According to the composition of one embodiment of the present invention, the strain can be *Lactobacillus reuteri* strain, and preferably *Lactobacillus reuteri* CH53 strain (Accession number: KCTC13149BP), but it is not limited thereto.

The cosmetic composition for skin moisturization of the present invention may further contain, other than the strain of the present invention or a culture solution of the strain, a well-known component for skin moisturization. When a material helpful for skin health is additionally included, the effect of the cosmetic composition for skin moisturization of the present invention would be further enhanced, and, when a material helpful for skin health is added, skin safety, easiness of formulation, stability of effective components, or the like that are associated with combined use may have to be considered.

The present invention still further provides a method for producing 1,3-propanediol comprising culturing the aforementioned strain.

The method for producing 1,3-propanediol of the present invention may also include a step of recovering 1,3-propanediol from a culture solution of the strain. For the step of recovering 1,3-propanediol from a culture solution of the strain, a common technique for separation, for example, distillation, electric dialysis, filtering evaporation, chromatography, solvent extraction, reaction extraction, or the like, may be used. In general, to separate a material with high purity, they may be used in combination.

As for the method of culturing the strain of the present invention, culturing can be carried out according to a method that is commonly used in the pertinent art, and it is not limited to any particular method.

Hereinbelow, the present invention will be described in detail with reference to the examples. However, it is evident that the following examples are given only for the purpose of exemplification of the present invention and the scope of the present invention is not limited to the following examples.

EXAMPLES

Example 1. Isolation of *Lactobacillus reuteri* CH53 Strain as Novel Lactic Acid Bacterium From a pig slaughterhouse in Iksan, Chollabuk-Do, South Korea, small intestine and duodenum samples were collected, and then 1 g of finely chopped samples was suspended in 10 mL of physiological saline and diluted $1 \times 10^{-4}$ fold. Then, after spreading the resultant on MRS solid medium containing bromocresol purple (10 g/L proteose peptone NO. 3, 10 g/L beef extract, 5 g/L yeast extract, 20 g/L dextrose, 1 g/L polysorbate 80, 2 g/L ammonium citrate, 5 g/L sodium acetate, 0.1 g/L magnesium sulfate, 0.05 g/L manganese sulfate, 2 g/L dipotassium phosphate, 0.04 g/L bromocresol purple, and 15 g/L agar), in an amount of 100 µl for each sample, it was cultured in anaerobic state for 24 hours at 37° C. by using Bactron Anaerobic Chamber (SHEL LAB, Cornelius, Oreg., USA). Colonies obtained after the culture were re-inoculated to an MRS medium containing bromocresol purple followed by separation. Accordingly, 81 kinds of *Lactobacillus reuteri* strain were separated by using MALDI Biotyper (Bruker Daltonik, Billerica, Mass., USA). Thus-separated 81 kinds of the colonies were inoculated to 3 mL MRS medium (in 15 mL Falcon tube) and then subjected to pre-culture in anaerobic state for 24 hours at 37° C. by using Bactron Anaerobic Chamber. After that, they were cultured, in 50 mL 1,3-propanediol production medium (20 g/L glycerol, 10 g/L proteose peptone NO. 3, 10 g/L beef extract, 5 g/L yeast extract, 20 g/L dextrose, 1 g/L polysorbate 80, 2 g/L ammonium citrate, 5 g/L sodium acetate, 0.1 g/L magnesium sulfate, 0.05 g/L manganese sulfate, and 2 g/L dipotassium phosphate) (250 mL round flask), in anaerobic state for 24 hours at 37° C. by using Bactron Anaerobic Chamber with initial inoculation OD of 0.5. At every 6 hours, 1 mL of the culture medium was collected and centrifuged for 5 minutes at 13,000 rpm, and then the supernatant was filtered through a 0.22 µm filter and analyzed by high performance liquid chromatography. Production amount of 1,3-propanediol was analyzed by high performance liquid chromatography at conditions using liquid flow rate of 6 mL/min, 0.25 mM $H_2SO_4$ as a mobile phase, an ion exchange column (300×78 mm, Aminex HPX-87H, Bio-Rad), and refractive index detector (RID).

As a result, among the 81 types of the stains in total, 4 strains were found to be capable of producing 1,3-propanediol. In addition, as a result of analyzing the culture sample of a strain which showed production of 1,3-propanediol at the 18$^{th}$ hour of the culture, *Lactobacillus reuteri* CH53 strain consumed the highest amount of glycerol, i.e., 20.1 g/L, to finally produce 16.3 g/L of 1,3-propanediol, and the production yield relative to glycerol was found to be 0.81 g/g (1,3-propanediol/glycerol). These results represent very high conversion rate of 98% compared to theoretical yield (0.83 g/g).

TABLE 1

Production of 1,3-propanediol by lactic acid bacterium *Lactobacilus reuteri* CH53 strain isolated in the present invention

| Strain | Production amount of 1,3-propanediol (g/L) | Glucose consumption amount (g/L) | Glycerol consumption amount (g/L) | Production yield (g/g) |
|---|---|---|---|---|
| *Lactobacillus reuteri* CH21 | 11.6 | 20.3 | 15.6 | 0.74 |
| *Lactobacillus reuteri* CH48 | 9.8 | 20.3 | 12.5 | 0.78 |
| *Lactobacillus reuteri* CH53 | 16.3 | 20.3 | 20.1 | 0.81 |
| *Lactobacillus reuteri* CH74 | 10.1 | 20.3 | 13.5 | 0.75 |

For final molecular biological identification of *Lactobacillus reuteri* CH53 strain showing the highest production of 1,3-propanediol, gene sequence of 16S rRNA was analyzed. From a single colony, chromosomal DNA was separated using a kit for extracting genomic DNA (Invitrogen, Germany). From the separated chromosomal DNA, DNA of 16S rRNA gene was amplified by using a primer set including 5'-AGAGTTTGATCMTGGCTCAG-3' (27f, SEQ ID NO: 1) and 5'-TACGGYTACCTTGTTACGACTT-3' (1492r, SEQ ID NO: 2), which are the primers for amplifying *lactobacillus* 16S rRNA gene. PCR amplification was carried out, after preparing a PCR reaction solution (50° C.) containing ExTaq polymerase (Takara) (2.5 U), polymerase buffer, dNTP mixture (each at 1 mM), each primer (100 pmol, 1 µl), and template DNA (500 ng), 30 times at conditions including 30 seconds at 96° C., 1 minute at 50° C., and 2 minutes at 72° C. using a gene amplifier (Takara, Japan). After confirming by electrophoresis of the PCR reaction solution on 1% agarose gel that the DNA fragment with expected size is amplified, transformation of *E. coli* EPI300 was carried out by using pGEM-TEasy vector (Promega, USA). From the transformed recombinant *E. coli*, the plasmid DNA was extracted (Qiagen, USA), and, according to a treatment with the restriction enzyme EcoRI, cloning of a DNA fragment with desired size was confirmed followed by nucleotide sequencing. On the basis of the results of performing the nucleotide sequence homology search, the separated *lactobacillus* was named as "*Lactobacillus reuteri* CH53."

Example 2. Production of 1,3-Propanediol Using Fermentation Tank Based on Fed-Batch Culture of *Lactobacillus reuteri* CH53 Strain as Newly Separated *Lactobacillus*

Investigation was made to see the production amount of 1,3-propanediol and by-products during fed-batch culture of *Lactobacillus reuteri* CH53 strain in MRS medium containing glycerol in 5-L incubator (20 g/L glycerol, 10 g/L proteose peptone NO. 3, 10 g/L beef extract, 5 g/L yeast extract, 20 g/L dextrose, 1 g/L polysorbate 80, 2 g/L ammonium citrate, 5 g/L sodium acetate, 0.1 g/L magnesium sulfate, 0.05 g/L manganese sulfate, and 2 g/L dipotassium sulfate). As a result, at the 54$^{th}$ hour of the culture, 1,3-propanediol was finally produced at 57.5 g/L, and the production yield of 1,3-propanediol from glycerol and productivity per hour were shown to be 0.815 g/g and 1.06 g/L/h, respectively. Furthermore, the production amount of by-products was as follows: lactic acid at 43.8 g/L, acetic acid at 17.1 g/L, and ethanol at 4.7 g/L.

Example 3. Production of 1,3-Propanediol Based on Fed-Batch Culture Method Optimized to *Lactobacillus reuteri* CH53 Strain as Newly Separated *Lactobacillus*, and Comparison of 1,3-Propanediol Productivity with Other Strains Culture solution containing *Lactobacillus reuteri* CH53, which has been pre-cultured for about 16 hours at 30° C. in 1-L round flask in which 100 mL MRS containing glycerol is included, was inoculated at a concentration of 10% (v/v) to a growth vessel, and then fed-batch culture was carried out in a 5-L vessel system under stirring which contains 3 L of MRS including glycerol. All fermentation experiments were carried out at 37° C. without aeration (i.e., no application of air or nitrogen gas, only with stirring), and pH was maintained at 5.5±0.2 by using 28% (w/v) NH$_4$OH or 2 M HCl. Determination was made with cell culture at stirring rate of 100 rpm, and all the results were obtained as a mean value of 3 independent tests. To enhance the 1,3-propanediol productivity, the above method was carried out with a slight modification of the method of Example 2.

As a result, it was found that, for producing 1,3-propanediol from glycerol, *Lactobacillus reuteri* CH53 strain (Accession number: KCTC13149BP) of the present invention shows the production amount of 65.5 g/L (based on 54 hours) and productivity per hour of 1.17 g/L/h. Thus, it was able to confirm that *Lactobacillus reuteri* CH53 strain (Accession number: KCTC13149BP) of the present invention is a strain which is more effective than other *lactobacillus* strains for producing 1,3-propanediol from glycerol.

TABLE 2

Comparison of productivity of 1,3-PDO from glycerol among other *Lactobacilus reuteri* strains

| Strain | 1,3-PDO (g/L) | Yield (g/g) | Fermentation method | Productivity (g/L/h) | Reference |
|---|---|---|---|---|---|
| *L. reuteri* ATCC 55730 | 65.3 | 0.80 | Fed-batch | 0.47 | Jolly et al., (2014) |
| *L. diolivorans* DSM 14421 | 85 | 0.53 | Fed-batch | 0.45 | Stefanet al., (2014) |
| *L. diolivorans* DSM 14421 | 85.4 | 0.47 | Fed-batch | 0.60 | Stefanet al., (2012) |
| *L. panis* PM1 | 16.23 | 0.72 | Batch | 0.08 | Kang et al., (2014) |
| *L. reuteri* DSM 20016 | 46 | 0.71 | Fed-batch | 0.92 | Mariaet al., (2015) |
| *L. reuteri* ATCC 55730 | 11 | 0.37 | Batch | 0.79 | Hema et al., (2011) |
| *L. diolivorans* DSM 14421 | 92 | 0.78 | Fed-batch | 0.56 | Katharina et al., (2017) |
| *L. reuteri* CH53 | 65.5 | 0.82 | Fed-batch | 1.17 | This study |

*Lactobacillus reuteri* CH53 strain was deposited in the Korea Research Institute of Bioscience and Biotechnology (having the address of 181, Ipsin-gil, Jeongeup-si, Jeollabuk-do 56212, Republic of Korea under the Access number of KCTC 13149BP on Nov. 8, 2016. The deposit has been made under the terms of the Budapest Treaty and all restrictions imposed by the depositor on the availability to the public of the biological material will be irrevocably removed upon the granting of a patent.

A sequence listing electronically submitted with the present application on May 16, 2019, an ASCII text file named 20190516_Q10519GR05_TU_SEQ.txt, created on May 3, 2019 and having a size of 1 K bytes, is incorporated herein by reference in its entirety.

The invention claimed is:

1. A method for producing 1,3-propanediol, the method comprising culturing a strain in a culture medium comprising glycerol, thereby converting the glycerol into 1,3-propanediol,
    wherein the strain is *Lactobacillus reuteri* CH53 strain deposited with Korea Research Institute of Bioscience and Biotechnology and having Accession number KCTC13149BP.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agagtttgat cmtggctcag                                    20

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
tacggytacc ttgttacgac tt                                 22